US00PP32519P3

(12) United States Plant Patent
Danziger

(10) Patent No.: US PP32,519 P3
(45) Date of Patent: Nov. 24, 2020

(54) ***GYPSOPHILA* PLANT NAMED 'DGYPMILSII'**

(50) Latin Name: *Gypsophila paniculata*
Varietal Denomination: DGYPMILSII

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/602,149

(22) Filed: Aug. 14, 2019

(65) Prior Publication Data

US 2020/0068768 P1 Feb. 27, 2020

(30) Foreign Application Priority Data

Aug. 23, 2018 (EC) ..... 1528-18

(51) Int. Cl.
*A01H 5/02* (2018.01)
*A01H 6/30* (2018.01)
*A01H 6/00* (2018.01)

(52) U.S. Cl.
USPC ..... Plt./354
CPC ..... *A01H 6/00* (2018.05); *A01H 5/02* (2013.01)

(58) Field of Classification Search
USPC ..... Plt./263.1, 354
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Gypsophila* cultivar named 'DGYPMILSII' is disclosed, characterized by medium-small size, semi-double flower, with a diameter around 6 mm and a broad, open inflorescence. The new variety is a *Gypsophila*, suitable for cut flower production and outdoor garden or container uses.

2 Drawing Sheets

Latin name of the genus and species: *Gypsophila paniculata.*

Variety denomination: 'DGYPMILSII'.

BACKGROUND OF THE INVENTION

The new *Gypsophila* cultivar is a product of chance discovery by the inventor, Gavriel Danziger. The new variety was discovered as a single plant seedling growing in a cut flower field of existing unnamed, unpatented *Gypsophila paniculata* varieties in Moshav Mishmar-Hashiva, Israel, in April 2013.

Asexual reproduction of the new cultivar 'DGYPMILSII' was first performed by basal vegetative cuttings during June of 2015, at a greenhouse in Moshav Mishmar-Hashiva, Israel. Subsequent propagation has shown that the unique features of this cultivar are stable and reproduced true to type in multiple successive generations.

SUMMARY OF THE INVENTION

The cultivar 'DGYPMILSII' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DGYPMILSII' These characteristics in combination distinguish 'DGYPMILSII' as a new and distinct *Gypsophila* cultivar:

1. Medium-small flower diameter around 6 mm.
2. Semi-double flower.
3. Broad, open inflorescence structure.

PARENT COMPARISON

The new variety was discovered as a chance seedling among several unnamed *Gypsophila.*

COMMERCIAL COMPARISON

Plants of the new cultivar 'DGYPMILSII' can be compared to the commercial variety *Gypsophila* 'DANGYPMINI', U.S. Plant Pat. No. 10,964. The varieties are similar in most horticultural characteristics; however, 'DGYPMILSII' differs in the following:

1. The new variety has larger flowers than this comparator.

Plants of the new cultivar 'DGYPMILSII' can also be compared to the variety *Gypsophila* 'DGYPCOSMIC', U.S. Plant Pat. No. 29,525. These varieties are similar in most horticultural characteristics; however, 'DGYPMILSII' differs in the following:

1. The new variety has semi-double flowers, while this comparator has full flowers.

BRIEF DESCRIPTION OF THE PHOTOGRAPHS

Figure 1:
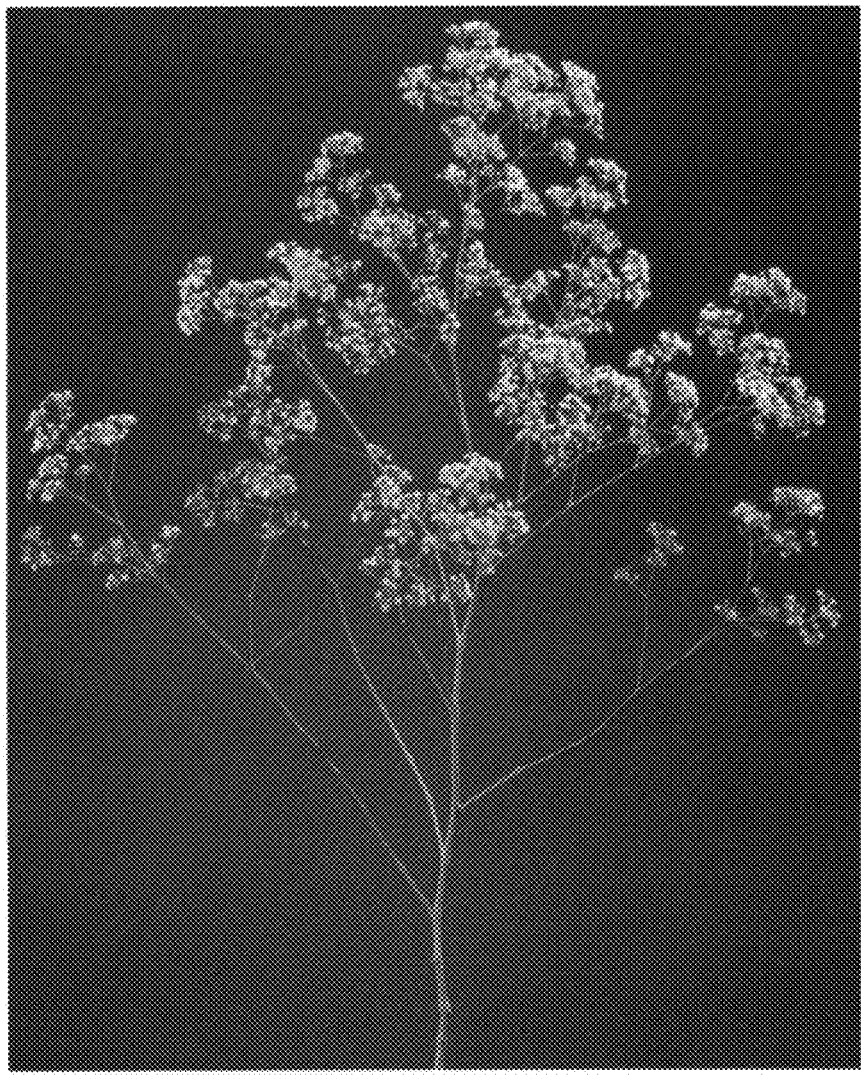

The accompanying photograph in FIG. 1 illustrates in full color a flowering stem of 'DGYPMILSII' grown outdoors in Moshav Mishmar-Hashiva, Israel.

Figure 2:
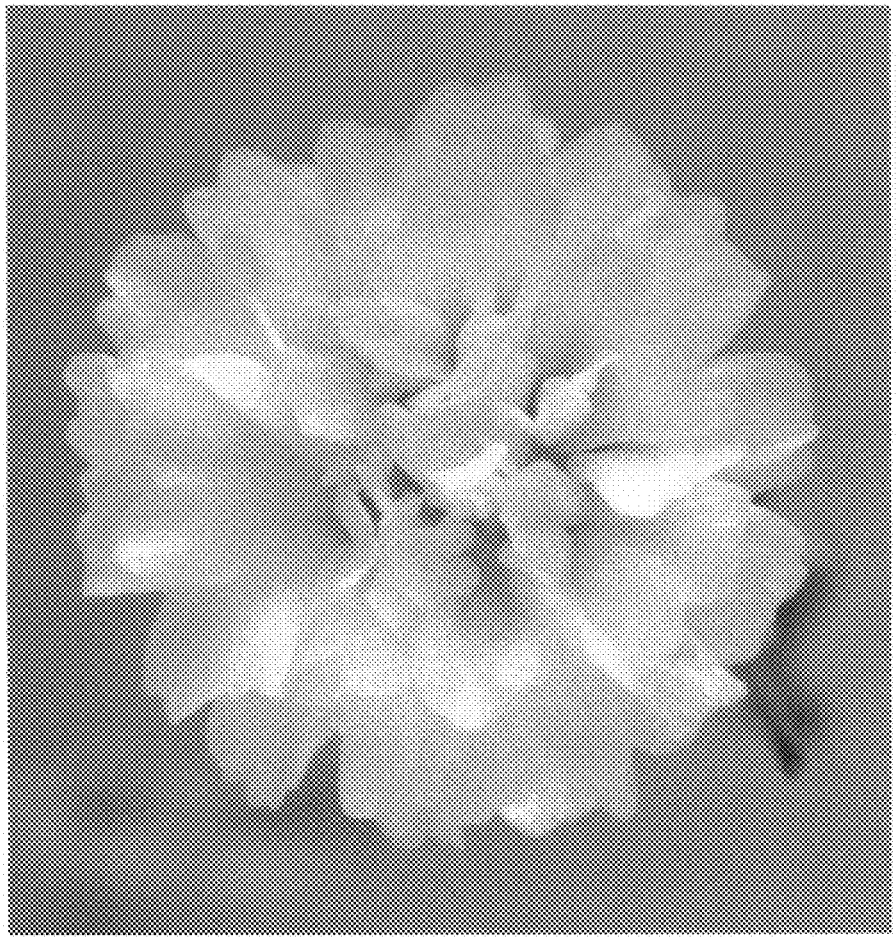

FIG. 2 illustrates in full color a close up view of flowers of 'DGYPMILSII'.

Plants in the photographs are approximately 4 months old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DGYPMILSII' plants grown in a greenhouse in Moshav Mishmar-Hashiva, Israel. Measurements were taken during Spring of 2015. The plants were approximately 4 months old. The growing temperature ranged from approximately 12° C. to 25° C. day and night. Measurements and numerical values represent averages of typical plant types.

Botanical classification: *Gypsophila paniculata* 'DGYPMILSII'

Propagation:

*Typical propagation material.*—Vegetative cuttings.

*Time to rooting.*—21 to 28 days at approximately 20° C.

*Root description.*—White and fibrous. Color not accurately measured with RHS color chart.

Plant:

*Growth habit.*—Upright.

*Height.*—Approximately 100 cm.

*Plant spread.*—Approximately 80 cm.

*Branching characteristics.*—Basal branch and side branches along the main branch.

*Length of lateral branches.*—Approximately 40 cm.

*Approximate quantity of lateral branches.*—Approximately 8.

*Diameter of lateral branches.*—Approximately 0.3 cm.

*Texture of lateral branches.*—Smooth.

*Lateral branch strength.*—Strong and flexible.

*Lateral branch color.*—Near RHS Yellow-Green 146D.

*Internode length.*—Average 5 cm.

*Age of plant described.*—Approximately 18 weeks.

Foliage:

*Leaf.*—Arrangement: Opposite. Compound or single: Compound. Shape of blade: Acuminate. Average Length: Approximately 6 cm. Average Width: Approximately 1.6 cm. Apex: Sharply acuminate. Base: Truncate. Attachment: Decurrent. Margin: Entire. Texture of top surface: Rough. Texture of bottom surface: Rough. Color: Young foliage upper side: Near RHS Yellow-Green 147A. Young foliage under side: Near RHS Yellow-Green 147A. Mature foliage upper side: Near RHS Yellow-Green 147A. Mature foliage under side: Near RHS Yellow-Green 147A. Venation: Type: Parallel. Venation color upper side: Near RHS Yellow-Green 147A. Venation color under side: Near RHS Yellow-Green 147B.

Flower:

*Bloom period.*—Natural Season: Spring to Summer. Greenhouse Production: Approximately 18 weeks.

*Inflorescence.*—Type: Clusters. Height: Approximately 90 cm. Width: Approximately 50 cm. Quantity of flowers per inflorescence/umbel: Approximately 1500.

*Bud.*—Bud shape: Oblate. Bud length: Approximately 0.1 cm. Bud diameter: Approximately 0.2 cm. Bud color: RHS Yellow-Green 146B, with White 155B. Base/calyx: RHS Yellow-Green 146B, with White 155B.

*Individual flower.*—Shape: Rounded. Quantity of flowers and buds per plant: Approximately 4500. Diameter of entire flower: Approximately 0.6 cm. Depth of flower: Approximately 0.2 cm. Rate of opening: Individual flowers: Fully open approximately 6 days from the bud stage. Cut Flower, longevity in vase: Approximately 12 days. Persistent or self-cleaning: Persistent. Fragrance: Soft.

*Petals.*—Length of petal: Approximately 0.4 cm. Width of petal: Approximately 0.15 cm. Apex: Sinuate. Shape of petal: Spatulate. Petal margin: Entire. Petal Arrangement: Rosette. Petal Number: Approximately 46. Petals Fused: Only at the base. Petal Appearance: Spatulate. Petal Texture: Smooth, all surfaces.

*Color.*—Upper surface at first opening: Near RHS White 155C. Upper surface at maturity: Near RHS White 155C. Upper surface at fading: Near RHS White 155B. Under surface at first opening: Near RHS White 155C. Under surface at maturity: Near RHS White 155C. Under surface at fading: Near RHS White 155B.

*Petaloids or other floral structures.*—None.

Sepal:

*Number.*—5.

*Sepal arrangement.*—Campanulate.

*Sepal length.*—Approximately 0.2 cm.

*Sepal width.*—Approximately 0.1 cm.

*Sepal shape.*—Lanceolate.

*Base.*—Acute.

*Apex shape.*—Apiculate.

*Margin.*—Entire.

*Color.*—RHS Yellow-Green 146B along margins, with White 155B.

*Sepal texture.*—Slightly rough.

Peduncle:

*Length.*—Approximately 0.8 cm.

*Diameter.*—Approximately 0.1 cm.

*Angle.*—About 45°.

*Strength.*—Good, flexible.

*Color.*—Near RHS Yellow-Green 146D.

Pedicel:

*Length.*—Approximately 0.5 cm.

*Diameter.*—Approximately 0.05 cm.

*Angle.*—Approximately 45°.

*Strength.*—Good, strong.

*Color.*—Near RHS Yellow-Green 146B.

Reproductive organs:

*Number of pistils per flower.*—2.

*Pistil Length.*—Approximately 0.5 cm.

*Stigma shape.*—Cannot be seen.

*Stigma color.*—Near RHS White 155C.

*Style color.*—Near RHS White 155C.

*Style length.*—Approximately 0.4 cm.

*Ovary color.*—Near RHS Yellow-Green 146D.

*Stamens quantity.*—Cannot be seen.

Other characteristics:

*Fruit/seed production.*—Kidney-shaped, colored near RHS Brown N200A. Seeds approximately 1-2 mm in diameter and 2-3 mm in length.

*Disease/pest resistance.*—As common to *Gypsophila*. Some observed tolerance to powdery mildew.

*Drought tolerance and cold tolerance.*—Quite good as common to *Gypsophila*.

*Temperature tolerance.*—USDA zones 3-9.

What is claimed is:

1. A new and distinct cultivar of *Gypsophila* plant named 'DGYPMILSII' as herein illustrated and described.

* * * * *